United States Patent [19]

Rhodes et al.

[11] 3,940,614

[45] Feb. 24, 1976

[54] METHOD AND APPARATUS FOR COLLECTION AND ANALYSIS OF MERCURY IN THE ATMOSPHERE

[75] Inventors: John R. Rhodes, Austin; David H. Weinstein, Brookshire; Andrzej H. Pradzynski, Austin, all of Tex.

[73] Assignee: Columbia Scientific Industries Corporation, Austin, Tex.

[22] Filed: Jan. 21, 1974

[21] Appl. No.: 434,774

[52] U.S. Cl............. 250/273; 250/272; 250/432 R; 250/492 R
[51] Int. Cl. ......................................... G01n 23/00
[58] Field of Search .......... 250/272, 273, 304, 432, 250/492

[56] References Cited
UNITED STATES PATENTS

| | | | |
|---|---|---|---|
| 3,173,016 | 3/1965 | Williston et al. | 250/218 |
| 3,309,518 | 3/1967 | Weiss | 250/273 |
| 3,612,859 | 10/1971 | Schumacher | 250/272 |

OTHER PUBLICATIONS

"A Simple Mercury Vapor Detector for Geochemical Prospecting," by W. W. Vaughn, Geological Survey Circular 540-1967, pp. 1–8.

"An Instrumental Technique for the Determination of Sub–microgram Concentrations of Mercury in Soils, Rocks, and Gas," by Vaughn et al., U.S. Geological Survey Prof. Paper 501D, pp. D123–D127, 1964.

*Primary Examiner*—James W. Lawrence
*Assistant Examiner*—B. C. Anderson
*Attorney, Agent, or Firm*—Arnold, White & Durkee

[57] ABSTRACT

Method and apparatus for detection of mercury vapor present in environmental atmosphere for the purpose of detecting the degree of environmental mercury pollution that might be present. Environmental air is passed through a bed of fibrous material such as glass wool, the fibers of which are coated with a noble metal, such as silver, capable of extracting mercury vapor from the environmental air. The bed of fibrous material may be placed within a heating chamber where sufficient heat is applied to drive off the collected mercury and a clean and perhaps inert gasiform fluid, such as clean air, nitrogen, argon, etc. is passed through the heating chamber to serve as a carrier for mercury vapor that is driven off of the bed of fibrous material. The mercury vapor laden carrier gas is then cooled and the mercury vapor present in the gas is collected by passing the gas through a screen of nylon mesh that is also coated with the noble metal. The mercury vapor that is collected by the coated nylon mesh may be analyzed with an x-ray fluorescence spectrometer capable of accurately detecting and measuring the amount of mercury present in the sample. The mercury vapor, after being driven off the bed of fibrous material, may be cooled and transported directly through a gas analyzer, such as a flameless atomic absorption analyzer with a mercury lamp, for ultra-violet absorption using the 2357A mercury line.

13 Claims, 2 Drawing Figures

METHOD AND APPARATUS FOR COLLECTION AND ANALYSIS OF MERCURY IN THE ATMOSPHERE

FIELD OF THE INVENTION

This invention relates generally to detection of mercury vapor present in air and more particularly is directed to a method and apparatus for accurately determining the amount of mercury vapor present in the environmental atmosphere for the purpose of detection of atmospheric pollution by detecting mercury vapor concentrations in industrial environments.

BACKGROUND OF THE INVENTION

In the field of medicine related to the effects of air pollution, it has been determined that mercury vapor can be harmful to the health of certain individuals if found in excessive concentrations in the atmosphere. It is considered practicable to utilize a method and apparatus for detection of mercury vapor pollution for the purpose of locating sources of mercury vapor pollution in order that such pollution may be controlled.

Three techniques are concurrently in use for determination of mercury vapor in atmosphere which are: (1) ultraviolet absorption (using the characteristic 2537 A mercury line) (various versions), (2) amalgamation followed by ultraviolet absorption, and (3) correlation spectrometry.

The detection limit of the simple resonant absorption methd is about 1 ng of mercury vapor in a 15 inch air path. This corresponds to roughly 1 ng/liter, which is 2 to 3 orders of magnitude higher than background concentrations. There is also even present the question of potential interference from other ultraviolet absorbers in the sample, such as water vapor, carbon dioxide, sulfur dioxide, hydrogen sulfide and various oxides of nitrogen. Although resonant absorption by mercury vapor is extremely selective, the concentrations of these other gases and vapors can be several orders of magnitude higher than that of the mercury vapor. Such interference has been found to present severe problems.

In an attempt to overcome these problems airborne survey work, where mercury vapor is detected by mercury detection equipment aboard aircraft, a refinement of the absorption technique has been utilized for accomplishing direct measurements in ambient air. Interference is minimized by utilizing the pressure broadening of the characteristic line emitted by a specific mercury vapor lamp. The cold vapor in the absorption path attenuates only the center portion of the line, whereas other ultraviolet absorbers attenuate the line entirely. The ratio of the signal from the center to that from the edges of the line is then obtained to reject interference. The resulting instrumentation is much more complex than a simple absorption cell, requiring precise temperature control of the lamp and special techniques to stabilize the photomultiplier detectors against drift relative to each other. A folded lightpath is utilized to increase sensitivity and still the detection limit is greater than 10 ng per cubic meter. Light losses especially at the mirrors also become a problem. Another version of this approach is to use a magnetic field to produce Zeeman splitting of the line, and to use this effect instead of pressure broadening.

An attempt has been made to adapt the principal of correlation spectrometry to direct mercury vapor determination. In this method the detected absorption spectrum (which usually contains many peaks) is mixed with an analog of the spectrum from the desired components. The output is proportional to the concentration of the desired components, free from spectral interferences. This method has not proved especially successful for direct mercury vapor determination.

It is believed that sample concentration is necessary to achieve the desired analytical performance for accurate detection of mercury vapor in air. This being so, it is logical to attempt to selectively concentrate the mercury and so simplify the analysis stage. This has been accomplished in the past by utilizing the amalgamation method of mercury detection. When the amalgmation method is employed, the mercury is collected by drawing the air to be analyzed past a gold or silver ribbon or mesh having a weight of about 1 g and a surface area of about 50 square centimeters. The mercury vapor is subsequently released into the analysis cell by radio frequency heating. The amalgamation is specific for mercury and the collection and release efficiencies are quoted to be in the order of 100 percent, thus insuring a quantitative analysis. At the detection limit, 1 ng of mercury is collected from up to one cubic meter of air. The resulting concentration in the analysis cell is about 1 ng/liter, yielding an effective concentration factor of $10^3$.

Utilizing this technique, adequate sensitivity for field analysis of soil gas samples is reported using very simple instrumentation. For airborne surveys, however, it is desirable to attain a detection limit of about 1 ng per cubic meter and if the analyses are to be performed in real time, the available sample collection time must be in the order of 0.1 to 5 minutes, based on a resolution of up to a few miles at a flying speed of 80 miles per hour. This implies that at least one cubic meter of air must be drawn past the amalgamator per minute necessitating a flow rate some two to three orders of magnitude higher than the maximum quoted for insuring one hundred percent amalgamation efficiency (1 cubic foot per minute).

It is desirable to provide a method of mercury vapor detection based on a rapid one hundred percent efficient collection of mercury vapor from the atmosphere by amalgamation onto a material that is provided with a thin coating of a noble metal and by subsequently removing collected mercury from the noble metal in such manner that it can be detected by means of x-ray fluorescent analysis. It is desirable to provide for collection, transfer and analysis of the mercury vapor in such manner that all possibility of erroneously high readings due to interference from other components present in vastly greater concentrations are effectively removed. It is also desirable that the method of collection and transfer be as near one hundred percent efficient as possible thereby insuring a quantitative rather than qualitative determination.

It is therefore a primary object of the present invention to provide a novel method and apparatus for detecting and measuring mercury vapor content present in the atmosphere.

It is an even further object of the present invention to provide a novel method and apparatus for efficiently detecting and measuring mercury content in the atmosphere, which method may be efficiently accomplished through use of simple and inexpensive collection and testing apparatus.

Among the several objects of the present invention is noted the provision of a novel method and apparatus for detection of the presence and amount of mercury vapor in an atmospheric environment which, although utilizing a known amalgamation approach, incorporates a feature of cascading in mercury vapor collection that insures one hundred percent amalgamation efficiency.

Other and further objects, advantages and features of the present invention will become apparent to one skilled in the art upon consideration of the written specification, the appended claims and the annexed drawings. The form of the invention, which will now be described in detail, illustrates the general principles of the invention, but it is to be understood that this detailed description is not to be taken as limiting the scope of the present invention.

SUMMARY OF THE INVENTION

In one suitable form of the invention a collecting station may be provided that facilitates passage of a predetermined volume of environmental air through a detection chamber for a predetermined period of time in order to provide for collection of mercury vapor from the atmosphere. The collecting station, which may be either a static facility, such as a conventional high volume air sampler, or a locomotive collection station, such as might be carried by a land vehicle or an aircraft, may typically include a conventional filter that facilitates removal of coarse airborne particulate, insects and the like from the air being tested. After initial filtering, the air is conducted through a bed of fibrous material such as glass wool which is coated with a noble metal that facilitates effective separation of mercury vapor from the air. The bed of fibrous material is of sufficient thickness to insure collection of substantially one hundred percent of the mercury vapor from the air being tested.

After a predetermined volume of environmental air has been conducted through the fibrous mat, the mat may be removed from the collecting apparatus and may be placed within a controlled heat chamber, where it may be subjected to a temperature in the order of 150° to 250° C, thereby driving the mercury from the fibrous material in the form of mercury vapor. A clean gasiform fluid, such as clean air, nitrogen or argon, may be passed through the heating chamber during the heating process, thereby serving as a carrier for the mercury vapor that is released during the heating process.

The heated gas is then appropriately cooled and passed through a second bed of fiber-like material such as nylon mesh, also coated with a suitable noble metal which serves to collect all of the mercury vapor that has been released during the heating process. The bed of fiber-like material must be thin, i.e., having a total mass per unit area less than about 10mg/cm$^2$ in order for the X-ray fluorescence method to function with optimum sensitivity. After collection, the collected mercury vapor is analyzed with an x-ray fluorescence spectrometer that efficiently measures the mercury content of the sample.

BRIEF DESCRIPTION OF THE DRAWINGS

So that the manner in which the above recited features, advantages and objects of the present invention, as sell as others, which will become apparent, are attained and can be understood in detail, more particular description of the invention, briefly summarized above, may be had by reference to the embodiment thereof which is illustrated in the appended drawings, which drawings form a part of this specification.

It is to be noted, however, that the appended drawings illustrate only a typical embodiment of the invention and are therefore not to be considered limiting of its scope, for the invention may admit to other equally effective embodiments.

In the Drawings:

FIG. 1 is a sectional view of a typical high volume sampler that is modified in accordance with the present invention to facilitate extraction of mercury vapor from air being drawn through the sampler.

FIG. 2 is a partially schematic sectional view of transfer apparatus constructed in accordance with the present invention and teaching cascading transfer of mercury vapor during collection for measurement.

DESCRIPTION OF PREFERRED EMBODIMENT

Figure 1:
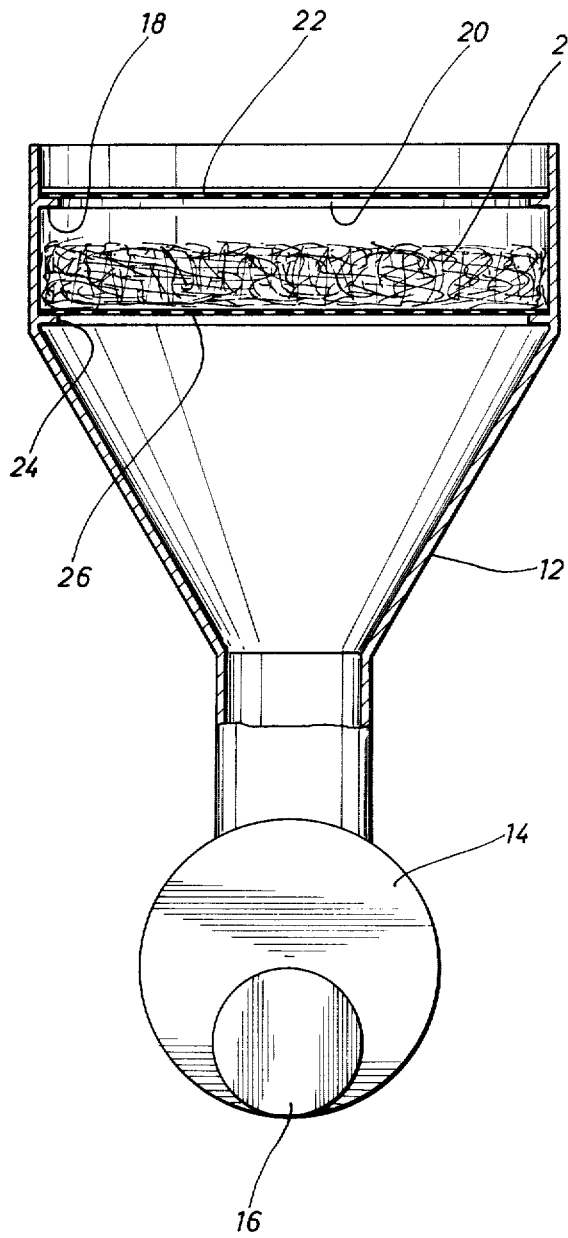

With reference now to FIG. 1, there is shown a typical high volume air sampler, generally at 10, that includes a housing 12 through which environmental air is drawn by a blower 14 that is powered by a suitable motor 16 such as an electric motor. The blower 14 is so constructed, relative to the size and operating speed of the motor 16 and relative to the size and configuration of the housing 12, to draw a predetermined volume of air through the housing 12 over a predetermined period of time. For example, the blower 14 may be capable of moving air through the housing 12 in the order of 40 to 70 cubic feet per minute, thereby giving the sampling apparatus the capability of detecting minute concentrations of mercury in the atmosphere in relatively short periods of sampling.

As is typically the case, the internal wall structure of the housing 12 may define a support shoulder 18 that is capable of supporting a filter screen 20 that, in turn, supports a filter membrane 22 that separates coarse particulate matter from the air along with various other airborne debris. Ordinarily, the filter membrane 22, after collection of the coarse material from the environment, is weighed and the weight compared to a pre-weight in order to determine the amount of solid particulate that is suspended in the air. It may be desirable, however, to provide a filter membrane that is utilized solely to prevent particulate matter from reaching the fibrous material.

It will be desirable, in order for mercury vapor to be extracted from the air being drawn through the high volume sampler 10, to provide, in addition to the filter membrane 22, a bed of material having a facility for extraction of mercury vapor. The bed of mercury extraction material, in order to insure substantially 100 percent extraction of the mercury, must be of predetermined thickness. In accordance with the present invention it has been determined that a fibrous material, if coated with a thin layer of a noble metal, such as silver or gold, will facilitate collection of mercury vapor from the air being drawn therethrough. Accordingly, the high volume sampler 12 may incorporate a lower support shoulder 24 that facilitates support of a support screen 26. The support screen provides support for a bed 28 of fibrous material such as glass wool that is made up of fibers that are thinly coated with a noble metal such as silver. Although mercury vapor amalgamates with a number of metals, particularly gold and silver, silver is preferred as the amalgamation material on the analytical mesh in both collection and transfer apparatus, primarily because silver characteristic x-rays do not interfere with the mercury x-rays whereas gold x-rays, for example, would constitute some degree or interference. It is not intended, however, to limit the scope of the present invention solely to the use of silver as an amalgamation metal in either or both of the cascading mercury vapor collection and transfer devices of the present invention.

In accordance with the present invention, silver is chemically deposited as a film in the order of 100 $\mu g/cm^2$ thick on the fibers of the fibrous material. Any one of a number of the conventional vapor methods of depositing silver on other materials, such as the fibers of the fibrous material, may be acceptable in accordance with the present invention. Silver is also preferred as a noble metal for the mercury vapor collector bed because the mercury vapor can be rapidly driven from the silver coated fibrous bed at a conveniently low temperature, in the order of 150° to 250° C for rapid and efficient transfer.

It is not intended to limit the scope of the present invention to use of any specific coated fibrous material as the vapor collector bed 28, but it has been determined that silver coated glass wool functions very efficiently as a mercury vapor collector bed. It has been determined that providing a 2 inch thick bed of silver loaded glass wool into a standard 4 inch diameter intake opening of a high volume sampler, thus forming a collector of an area in the order of 90 square centimeters, is an efficient mercury vapor collection bed for typical ambinet air sampling for mercury detection. A high volume sampler, having its intake opening with a two inch bed of silver coated glass wool has been demonstrated to have one hundred percent collection efficiency at a flow rate of 70 cubic feet per minute. Detection limits of 1 ng per cubic meter have been achieved using one hour collection time.

Figure 2:
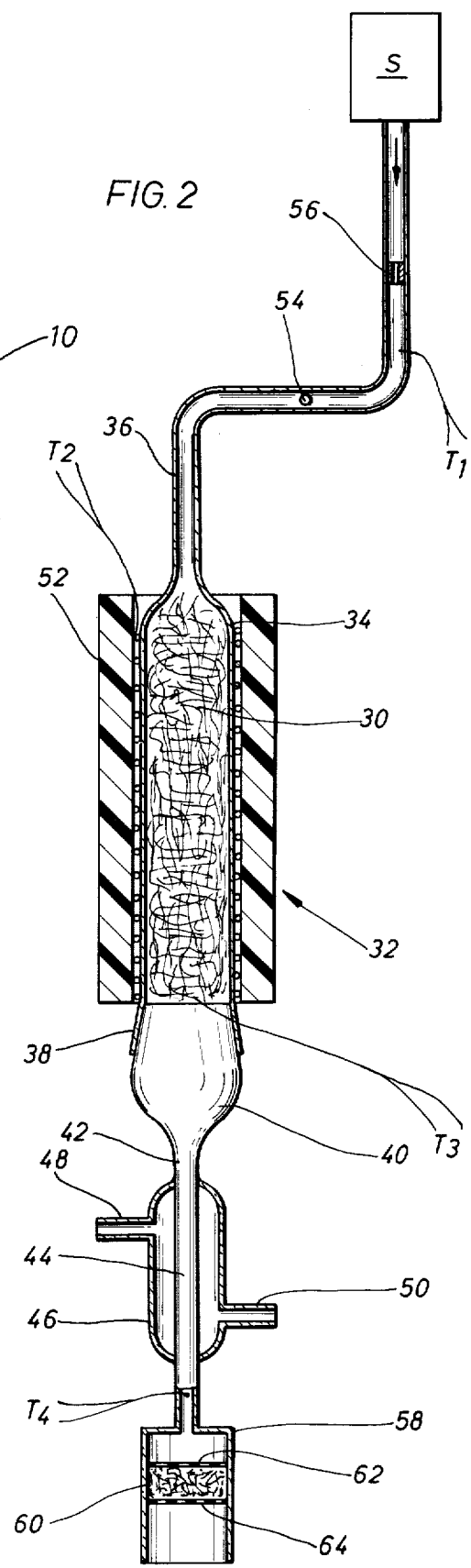

After proper collection has taken place, the silver loaded glass wool mat or bed, along with the entrapped amalgamated mercury vapor, may be removed from the high volume sampler and may be inserted into the heating chamber 30 of mercury vapor transfer apparatus, illustrated generally at 32 in FIG. 2. The heating chamber 30 may be defined by a large tubular conduit section 34 having a closed extremity connected to a tubular carrier gas supply conduit 36 and having a belled extremity 38 adapted to receive a closure element 40. The closure element is in turn connected by a conduit 42 to a cooling conduit 44 surrounded by a cooling jacket 46 that serves to cool the carrier gas and the vaporized mercury as it passes through the conduit 44. The cooling jacket 46 may be provided with connectors 48 and 50 that serve as inlet and outlet conduits for a cooling medium, such as water, being circulated through the cooling jacket 46.

For the purpose of driving mercury vapors from the silver loaded glass wool inserted within the chamber 30, it will be desirable to maintain the heating chamber at, but not above, an optimum heating level. As indicated above, collected mercury, in amalgamated form, will be driven from the silvered glass wool collector in the form of mercury vapor when elevated to a temperature of from 150° to 250° C. To insure maintenance of optimum temperature conditions in the heating chamber 30, the tubular wall structure 34 defining the heating chamber may be covered or wrapped with a heat source, such as electrical heater tape, or the heating chamber may be provided with a radio frequency heater coil. The heater tape or radio frequency heater coil may be appropriately energized to generate sufficient heat to maintain the heating zone within the predetermined operating range. Thermocouples T1, T2, T3 and T4 may be strategically located in order to detect the temperature in various parts of the process and may, if necessary, be utilized for controlling the degree of heat that is supplied to maintain the process within an optimum operating temperature range. An insulator 52 may be disposed about the tubular conduit 34 to prevent excessive loss of heat from the heating chamber 30. It is desirable that the mercury vapor cloud be released from the silver loaded glass wool at a rate not exceeding 40 $\mu g$ per minute because there is a possibility of condensation if this rate is exceeded.

Carrier gas may be conducted from a suitable source S into the carrier gas supply conduit 36. The flow of the carrier gas may be controlled by means of a flow meter 54 or may be controlled by passing the gas through a critical orifice 56 disposed within the conduit 36.

Downstream from the cooling jacket 46, the conduit 42 may be connected with a collection chamber 58 within which may be disposed a thin specimen, such as a nylon mesh material, that is also coated with a noble metal. The nylon mesh may be coated with the same noble metal with which the fibrous material is coated. A pair of support screens 62 and 64 may be disposed within the chamber 58 in order to support the thin specimen 60 in such a manner that the carrier gas passing from the conduit 42, after having been cooled, will flow into the chamber 58 and through the thin specimen, thereby allowing all of the mercury vapor carried thereby to be separated by amalgamation and become entrapped by the thin collector specimen.

The collector specimen 60 then may be removed from the collector chamber 58 and may be analyzed by direct measurement of the concentration of amalgamated mercury on the mesh by x-ray fluorescence analysis The sensitivity and speed of anlaysis is derived as follows:

An analytical detection limit of 10 $ng/cm^2$ (or better) in a minute count can be achieved by exciting HgL x-rays using a radioisotape source such as Pu-238 which emits UL x-rays which efficiently excite the mercury L x-rays. A high resolution Si (Li) detector may be used to count the HgL line. The measured area of coated mesh may be about 3 $cm^2$ so the absolute detection limit may be in the order of thirty ng. Thus, to achieve a detection limit in air of one ng per cubic meter in one minute's sampling time, thirty cubic meters of air must be passed through the collector in one minute. The required flow rate is thus some 1,180 cubic feet per minute. It has been determined that to maintain one hundred percent collection efficiency through a 2 inch thick bed of silver coated glass wool, the air velocity should not exceed approximately 6 meters per second. Assuming an air velocity of 5 meters per second, the collector area (for an 1,180 cubic foot per minute air flow rate) must be in the order of 1/10 square meters. Thus, a one foot square collector (900 square centimeters) would be suitable to maintain virtually one hundred percent collection efficiency. The mercury vapor collector may be airborne or it may be transported by a land vehicle in any suitable manner.

As indicated above, after collection, the silver loaded glass wool mat can be rolled up and inserted into the heating chamber 30 of the transfer apparatus and may there constitute a thickness of glass wool through which a heated gas such as clean air, nitrogen or argon is passed. All of the mercury is driven off from the glass wool mat in a few seconds at 150° to 250° C. The gas flow rate controlled by the flow meter 54 or the critical orifice 56 should be sufficiently slow (in the order of 2 liters per minute) to insure 100 percent efficiency on the thin mesh specimen 60 disposed downstream of the transfer apparatus.

If rapid collection is not required, a very simple collecting apparatus, consisting of a modified "high volume" commercially available air sampler, can be employed. The high volume air sampler may be modified simply by providing means for loading a two inch thick bed of appropriately coated glass wool into the standard four inch diameter input of the sampler, thus forming a collector area of ninety square centimeters. Sampler structure of this nature has been demonstrated to have one hundred percent collection efficiency at a flow rate of seventy cubic feet per minute and detection limits of 1 ng per cubic meter have been achieved employing a collection time of one hour.

The present invention is based upon rapid, 100 percent efficient collection of mercury vapor from the atmosphere by amalgamation onto a fibrous material such as glass wool that is provided with a thin coating of a noble metal, such as silver or gold. Subsequent to collection of mercury vapor by the coated fibrous material, the mercury is transferred to a thin specimen such as nylon mesh that is also coated with a noble metal which may be the same or a different noble metal from that with which the fibrous material is coated. Transfer of the mercury to the thin specimen is accomplished by application of heat to the glass wool and by passing a small volume of hot carrier gas through the gases wool to transport the released mercury to the thin specimen. The carrier gas is cooled immediately preceding contact with the thin specimen, thereby causing the mercury vapor carried thereby to readily become amalgamated with the noble metal coating of the thin specimen. Care must be taken to insure against exceeding the saturation vapor pressure of mercury in the region where the thin specimen is located. Measurement of the mercury then may take place by means of radioisotope x-ray fluorescence analysis of the mesh employing the "thin specimen technique" which gives the weight of the mercury directly.

The collection transfer and analysis techniques are highly specific for mercury, thus removing all possibility of erroneously high readings due to interference from other components present in vastly greater concentrations. Since the collection and transfer techniques are 100 percent efficient, quantitative determination is effectively insured.

In view of the foregoing, it is apparent that the present invention is one well adapted to attain all of the objects, hereinabove set forth, together with other advantages, which will become obvious and inherent from a description of the apparatus itself.

It will be understood that certain combinations and subcombinations are of utility and may be employed without reference to other features and subcombinations. As many possible embodiments may be made of this invention without departing from the spirit or scope thereof, it is to be understood that all matters herein set forth and shown in the accompanying drawings are to be interpreted as illustrative and not in a limiting sense.

What is claimed is:

1. A method of detecting and measuring the concentration of mercury vapor in the atmosphere, comprising the steps of:

forcing a measured volume of air containing an unknown concentration of mercury vapor through a first fibrous material coated with a noble metal, for a predetermined period of time, to produce a first mercury amalgam of said noble metal on the surface of said first fibrous material;

heating said first fibrous material so as to vaporize the mercury deposited thereon;

passing a carrier gas through said first fibrous material to transport said vaporized mercury from the surface thereof;

passing said carrier gas containing the vaporized mercury through a second fibrous material also coated with a noble metal;

cooling said carrier gas immediately prior to passing it through said second fibrous material, to produce a second mercury amalgam on the surface of said second fibrous material; and measuring the amount of mercury deposited on said second fibrous material by x-ray fluorescence analysis.

2. A method as recited in claim 1, wherein said noble metal on said first fibrous material is silver.

3. A method as recited in claim 1, wherein said noble metal on said first and said second fibrous material is silver.

4. A method as recited in claim 1, wherein said noble metal is chemically deposited as a film of approximately 100 micrograms per square centimeter on the fibers of both said first and said second fibrous material.

5. A method as recited in claim 1, wherein said first fibrous material is glass wool.

6. A method as recited in claim 1, wherein said first fibrous material is placed in a high volume sampler.

7. A method as recited in claim 1, wherein said first fibrous material is glass wool and said second fibrous material is nylon mesh.

8. A method as recited in claim 1, wherein the volume of said second fibrous material is smaller than the volume of said first fibrous material.

9. A method as recited in claim 1, wherein said second fibrous material has a mass per unit area of less than ten milligrams per square centimeter.

10. A method as recited in claim 1, wherein the mercury deposited on said first fibrous material is released at a rate not exceeding 40 nanograms per minute.

11. A method as recited in claim 1, wherein the saturation vapor pressure of mercury is not exceeded in cooling said carrier gas.

12. A method as recited in claim 1, wherein said transporting is by a heated carrier gas.

13. A method as recited in claim 1, wherein said carrier gas is clean air.

* * * * *

UNITED STATES PATENT OFFICE
CERTIFICATE OF CORRECTION

PATENT NO. : 3,940,614

DATED : February 24, 1976

INVENTOR(S) : John R. Rhodes, David H. Weinstein, & A. Pradzynski

It is certified that error appears in the above—identified patent and that said Letters Patent are hereby corrected as shown below:

Col. 1, line 24, "concurrently" should read --currently--.

Col. 1, line 31, "methd" should read --method--.
Col. 1, line 44, --for-- should be inserted after "problems".
Col. 3, line 66, "sell" should read --well--.
Col. 5, line 4, "or" should read --of--.

Signed and Sealed this twenty-ninth Day of June 1976

[SEAL]

Attest:

RUTH C. MASON
Attesting Officer

C. MARSHALL DANN
Commissioner of Patents and Trademarks